(12) United States Patent
Wada et al.

(10) Patent No.: US 9,346,748 B2
(45) Date of Patent: May 24, 2016

(54) FUNCTIONAL-GROUP-MODIFIED CARBON MATERIAL, AND METHOD FOR PRODUCING SAME

(71) Applicants: SEKISUI CHEMICAL CO., LTD., Osaka (JP); NIIGATA UNIVERSITY, Niigata (JP)

(72) Inventors: Takuya Wada, Osaka (JP); Norio Tsubokawa, Niigata (JP)

(73) Assignees: SEKISUI CHEMICAL CO., LTD., Osaka (JP); NIIGATA UNIVERSITY, Niigata (JP)

( * ) Notice: Subject to any disclaimer, the term of this patent is extended or adjusted under 35 U.S.C. 154(b) by 0 days.

(21) Appl. No.: 14/008,532

(22) PCT Filed: Nov. 20, 2012

(86) PCT No.: PCT/JP2012/080078
§ 371 (c)(1),
(2) Date: Sep. 27, 2013

(87) PCT Pub. No.: WO2013/080843
PCT Pub. Date: Jun. 6, 2013

(65) Prior Publication Data
US 2014/0080950 A1 Mar. 20, 2014

(30) Foreign Application Priority Data

Nov. 30, 2011 (JP) .................................. 2011-262157
Nov. 30, 2011 (JP) .................................. 2011-262158

(51) Int. Cl.
*C01B 31/04* (2006.01)
*C07C 265/02* (2006.01)
(Continued)

(52) U.S. Cl.
CPC ............... *C07C 265/02* (2013.01); *B82Y 30/00* (2013.01); *B82Y 40/00* (2013.01); *C01B 31/0484* (2013.01); *C07C 211/01* (2013.01); *C08K 5/17* (2013.01); *C08K 5/29* (2013.01)

(58) Field of Classification Search
CPC .................................................. C01B 31/0423
See application file for complete search history.

(56) References Cited

U.S. PATENT DOCUMENTS

2006/0038299 A1    2/2006  Hirakata et al.
2006/0083762 A1*   4/2006  Brun et al. ...................... 424/401
(Continued)

FOREIGN PATENT DOCUMENTS

CN           1587031 A       3/2005
CN         101294009 A   *  10/2008
(Continued)

OTHER PUBLICATIONS

Karousis (Porphyrin counter anion in imidazolium-modified graphene-oxide. Carbon, 2010, 48, pp. 854-860).*
(Continued)

*Primary Examiner* — Brieann R Fink
(74) *Attorney, Agent, or Firm* — Cheng Law Group, PLLC

(57) ABSTRACT

Provided are a functional-group-modified carbon material modified with an isocyanate group or amino group, and a method for producing the material. The material is an isocyanate-group-modified carbon material in which an isocyanate group of a diisocyanate compound is bonded to a graphene-like carbon material, or an amino-group-modified carbon material in which a fragment obtained by radical-decomposing an amino-group-containing azo-type radical initiator is added to the graphene-like carbon material by radical-trapping. The method is a method for producing a functional-group-modified carbon material, including heating and stirring, in a solvent, a graphene-like carbon material, and a diisocyanate compound or an amino-group-containing azo-type radical initiator.

5 Claims, 3 Drawing Sheets

(51) Int. Cl.
*C07C 211/01* (2006.01)
*C08K 5/17* (2006.01)
*C08K 5/29* (2006.01)
*B82Y 30/00* (2011.01)
*B82Y 40/00* (2011.01)

(56) References Cited

U.S. PATENT DOCUMENTS

2010/0096595 A1* 4/2010 Prud'Homme et al. ...... 252/500
2010/0193727 A1* 8/2010 Lee et al. ................ 252/62.55

FOREIGN PATENT DOCUMENTS

| | | |
|---|---|---|
| CN | 101386714 A | 3/2009 |
| CN | 102127324 A | 7/2011 |
| JP | 2004-162203 A | 6/2004 |
| JP | 2004-351602 A | 12/2004 |
| JP | 2005-508067 A | 3/2005 |
| JP | 2007-169112 A | 7/2007 |
| WO | WO-03/038837 A1 | 5/2003 |

OTHER PUBLICATIONS

Machine translated English equivalent of CN 101294009 (Oct. 2008, 5 pages).*

International Search Report for the Application No. PCT/JP2012/080078 mailed Jan. 15, 2013.

Written Opinion of the International Searching Authority (PCT/ISA/237) for Application No. PCT/JP2012/080078 mailed Jan. 15, 2013.

Luong, Nguyen Dang et al., "Enhanced mechanical and electrical properties of polyimide film by graphene sheets via in situ polymerization", Polymer, 2011, vol. 52, pp. 5237-5242.

Kim, Hyunwoo at al., "Graphene/polyethylene nanocomposites: Effect of polyethylene functionalization and blending methods", Polymer, 2011, vol. 52, pp. 1837-1846.

Ren, Peng-Gang et al., "Improved Properties of Highly Oriented Graphene/Polymer Nanocomposites", Journal of Applied Polymer Science, Sep. 15, 2011, vol. 121, No. 6, pp. 3167-3174.

Written Opinion of the International Searching Authority (PCT/ISA/237) for Application No. PCT/JP2012/080078 mailed Jan. 15, 2013 (English Translation mailed Jun. 12, 2014).

The First Office Action for the Application No. 201280029130.7 from The State intellectual Property Office of the People's Republic of China dated Feb. 11, 2015.

Stankovich, Sasha et al, "Synthesis and exfoliation of isoryanate-treated graphene oxide nanoplatelets", Carbon, 2006, vol. 44, pp. 3342-3347.

Murugesan, Sankaran et al., "Can Graphene be the Electrode Support for Pt in Formic acid Eleotrooxidation?", ECS Transactions, 2009, vol. 19, No. 5, pp. 249-257.

Zhang, Bin et al., "Poly(*N*-Vinylcarbazole) Chemically Modified Graphene Oxide", Journal of Polymer Science Part A: Polymer Chemistry, 2010, vol. 48, No. 12, pp. 2642-2649.

Compton, Owen C. et al., "Electrically Conductive "Alkylated" Graphene Paper via Chemical Reduction of Amine-Functionalizecl Graphene Oxide Paper", Advanced Materials, 2010, vol. 22, No. 8, pp. 892-896.

Nethravathi, C. et al., "Chemically Modified Graphene Sheets Produced by the Solvothermal Reduction of Colloidal Dispersions of Graphite Oxide", Carbon, Elsevier, 2008, vol. 46, No. 14, pp. 1994-1998.

Supplementary European Search Report for the Application No. EP 12 85 2901 dated Jul. 21, 2015.

Notification of Reasons for Refusal for the Application No. 2011-262157 from Japan Patent Office mailed Jan. 26, 2016.

Notification of Reasons for Refusal for the Application No. 2011-262158 from Japan Patent Office mailed Jan. 26, 2016.

* cited by examiner

FUNCTIONAL-GROUP-MODIFIED CARBON MATERIAL, AND METHOD FOR PRODUCING SAME

TECHNICAL FIELD

The present invention relates to a functional-group-modified carbon material in which a graphene-like carbon material such as exfoliated graphite is modified with an isocyanate group or amino group, and a method for producing the modified carbon material.

BACKGROUND ART

Hitherto, a carbon material, such as graphite, carbon nanotubes or carbon particles, has been widely used as an adsorbent, a wiring material, or a reinforcing agent or filler into a resin. In recent years, attention has been paid to exfoliated graphite, which is obtained by peeling off flakes from graphite and has a smaller number of graphene layers laminated than graphite.

When a carbon material as described above is used, the material is dispersed in a solvent or synthetic resin in many cases. However, exfoliated graphite, carbon nanotubes or the like is large in aspect ratio to cause a problem of being low in dispersibility therein. Patent Document 1 listed below discloses a modified carbon material in which a carbon material having a graphene sheet structure is heightened in dispersibility. Patent Document 1 discloses a modified carbon material obtained by adding a fragment obtained by radical-decomposing an azo-type radical polymerization initiator containing a carboxyl group to a carbon material having a graphene sheet structure, for example, vapor phase growth carbon fibers or carbon nanotubes. This modified carbon material has been made high in dispersibility in water by the modification with the carboxyl group.

PRIOR ART DOCUMENT

Patent Document

Patent Document 1: JP 2007-169112 A

SUMMARY OF THE INVENTION

Problems to be Solved by the Invention

In Patent Document 1, the above-mentioned carbon material, which is modified with a carboxyl group, is disclosed. In recent years, attempts have been made in which various reactive groups are added to a graphene-like carbon material, such as graphene or exfoliated graphite. By the addition of various reactive groups to a graphene-like carbon material, a composite material of the carbon material and a resin can be improved in physical properties.

An object of the present invention is to provide a functional-group-modified carbon material in which an isocyanate group or amino group is added to a graphene-like carbon material, and a method for producing the modified carbon material.

Means for Solving the Problems

To attain the object, the present inventors have made eager investigations to find out that a carbon material modified with an isocyanate group can be obtained by allowing a diisocyanate compound to react with a graphene-like carbon material. Thus, the present invention has been attained.

Additionally, to attain the object, the present inventors have also made eager investigations to find out that a carbon material modified with an amino group can be obtained by adding a fragment obtained by radical-decomposing an amino-group-containing azo-type radical initiator to a graphene-like carbon material by radical trapping. Thus, the present invention has been attained.

That is, the functional-group-modified carbon material according to the present invention is a material wherein an isocyanate group of a diisocyanate compound, or a fragment obtained by radical-decomposing an amino-group-containing azo-type radical initiator is bonded or added to a graphene-like carbon material.

The graphene-like carbon material to be preferably used is exfoliated graphite. Exfoliated graphite means a laminate of graphene that is obtained by peeling off flakes from ordinary graphite and that is a material in which the number of graphene layers laminated is from several to about 200 and the specific surface area is from about 600 to 2500 $m^2/g$.

When the graphene-like carbon material is exfoliated graphite, the material is large in specific surface area, and thus, physical properties and the like of a resin can be improved by a small addition amount of the material thereto.

In the method for producing an isocyanate-group-modified carbon material according to the present invention, a graphene-like carbon material, and a diisocyanate compound or amino-group-containing azo-type radical initiator are heated and stirred in a solvent. In this way, a functional-group-modified carbon material of the present invention can be obtained.

In the producing method of the present invention, the graphene-like carbon material to be preferably used is exfoliated graphite. In this case, it is possible to provide a carbon material capable of improving physical properties and the like of a resin by a small addition amount of the material thereto.

In the producing method of the present invention, the azo-type radical initiator to be preferably used is an azo-type radical initiator containing a secondary or tertiary amino group. As will be detailed later, in this case, an amino-group-modified carbon material can be effectively obtained only by heating and stirring in a solvent.

According to another specific aspect of the present invention, provided is a composite material including the functional-group-modified carbon material according to the present invention, and a resin. In a more specific aspect of the present invention, resin fine particles are used as the resin.

Effects of the Invention

In the functional-group-modified carbon material according to the present invention, graphene-like carbon is modified with an isocyanate group or amino group. Accordingly, by hydrolyzing the isocyanate group, an amine-modified graphene-like carbon material can easily be provided. Moreover, by allowing the isocyanate group to react with a hydroxyl group, a urethane bond can be formed. Accordingly, by allowing the isocyanate-group-modified carbon material of the present invention to react with a resin material having a hydroxyl group, such as a diol, a composite material can be provided which has physical properties of a urethane resin and is further improved in physical properties such as mechanical strength by graphene-like carbon.

In the amino-group-modified carbon material according to the present invention, a fragment obtained by radical-decomposing an amino-group-containing azo-type radical initiator is added to graphene-like carbon, and thus, a positively-charged graphene-like carbon material can be provided. It is therefore possible to provide a carbon material suitable for obtaining a composite material of the carbon material and, for example, negatively-charged resin fine particles.

Moreover, the method for producing a functional-group-modified carbon material according to the present invention makes it possible to provide a functional-group-modified carbon material as described above, which has conventionally failed to be obtained.

DESCRIPTION OF EMBODIMENTS

Figure 1:
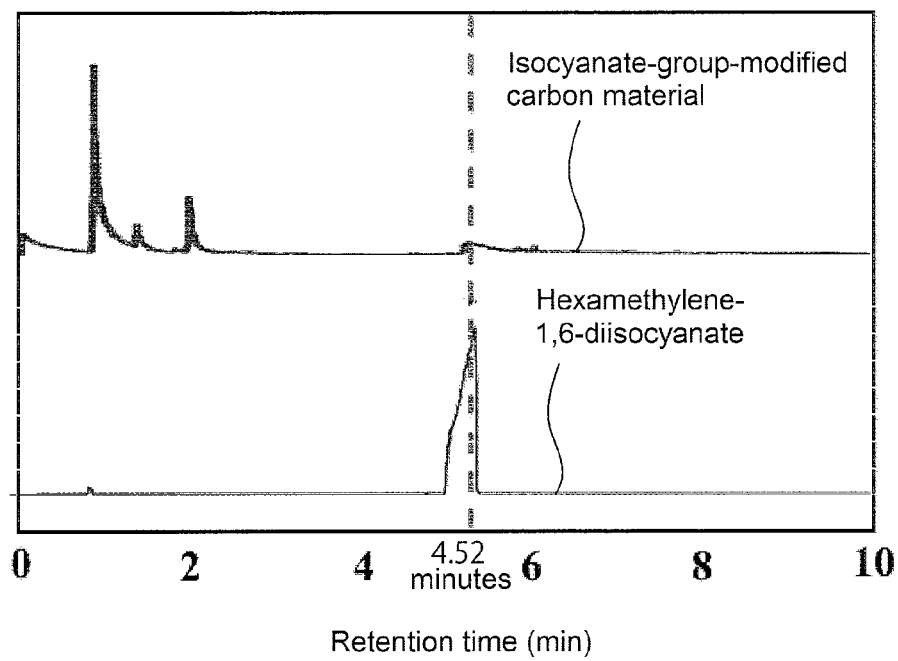
FIG. 1 is a chart showing chromatograms of respective thermal decomposition gases from an isocyanate-group-modified carbon material obtained in Example 1 and hexamethylene-1,6-diisocyanate.

Hereinafter, specific embodiments of the present invention will be described.

As the functional-group-modified carbon material according to the present invention, provided is an isocyanate-group-modified carbon material or amino-group-modified carbon material.

When the isocyanate-group-modified carbon material according to the present invention is obtained, a graphene-like carbon and a diisocyanate compound are heated and stirred in a solvent.

When the amino-group-modified carbon material according to the present invention is obtained, a graphene-like carbon and an amino-group-containing azo-type radical initiator are heated and stirred in a solvent.

(Graphene-Like Carbon Material)

The above-mentioned graphene-like carbon material that can be suitably used is graphene, or exfoliated graphite in which plural graphene layers are laminated. As described above, exfoliated graphite is graphite in which the number of graphene layers laminated is from several to about 200 so as to be smaller than in ordinary graphite. Exfoliated graphite is far larger in specific surface area than ordinary graphite. As described above, the area is from 600 $m^2/g$ or more and 2500 $m^2/g$ or less. Thus, only by adding a small amount of this material to a resin, the resultant can achieve a desired reinforcing effect, a physical-property improving effect, and the like.

The exfoliated graphite that may be used is any commercially available exfoliated graphite. The exfoliated graphite may be obtained by various treatments capable of peeling off flakes from graphite.

The method for obtaining exfoliated graphite as described above is not particularly limited. Thus, exfoliated graphite may be obtained by swelling graphite to obtain swelled graphite, and peeling off flakes from the resultant swelled graphite. For the step of swelling graphite to obtain swelled graphite, for example, the following can be used: 1) a method of immersing layered graphite into an acid solution to allow the acid solution to be taken between layers; or 2) an electrolysis method.

The method 1) is a method of immersing layered graphite into nitric acid or sulfuric acid, and heating the immersed graphite to intercalate nitrate ions or sulfate ions between layers. In this case, it is desired that the concentration of nitric acid and that of sulfuric acid are each from about 40 to 70% by weight. When the concentrations are each in this range, the nitrate ions or sulfate ions can be certainly intercalated between layers. If necessary, the solution may be stirred or heated. When the solution is an aqueous solution, the heating temperature is preferably in the range of 20° C. or higher and 95° C. or lower. When the temperature is in this range, the nitrate ions or sulfate ions can be certainly intercalated between layers.

In the electrolysis method 2), layered graphite is used as a working electrode, and the working electrode is immersed together with a counter electrode made of, for example, Pt into nitric acid or sulfuric acid to electrolyze the acid. In this way, electrolytic ions such as nitrate ions or sulfate ions can be intercalated between layers of the layered graphite, that is, between layers of graphene, so that gaps between layers can be widened.

Next, the sheet made of the swelled graphite obtained as described above is washed with, for example, water, and then dried at a low temperature to remove an excessive amount of the nitrate ions, sulfuric acid ions, or the like. In such a way, a dried sheet made of the swelled graphite can be obtained. In order to peel off flakes from the swelled graphite to give exfoliated graphite, a heating or ultrasonic-applying method or the like can be used.

The graphene-like carbon material in the present invention is not limited to graphene or exfoliated graphite, and various graphene-like carbon materials each having, on a surface thereof, a graphene sheet structure, such as carbon nanotubes may be used therefor.

(Isocyanate-Group-Modified Carbon Material)

The above-mentioned diisocyanate compound that can be used is, for example, hexamethylene diisocyanate (HMDI), tolylene diisocyanate, isophorone diisocyanate, or xylene diisocyanate.

The method for modifying the above-mentioned graphene-like carbon material with an isocyanate, which can be used, is a method of mixing the graphene-like carbon material with a diisocyanate compound in a solvent and then heating the mixture. In a specific example thereof, the graphene-like carbon material and hexamethylene diisocyanate are dispersed in a solvent, for example, toluene, and then the resultant is heated at a temperature of 80° C. In this way, an isocyanate-group-modified carbon material of the present invention can be obtained as shown in the following formula (1).

[Chemical formula 1]

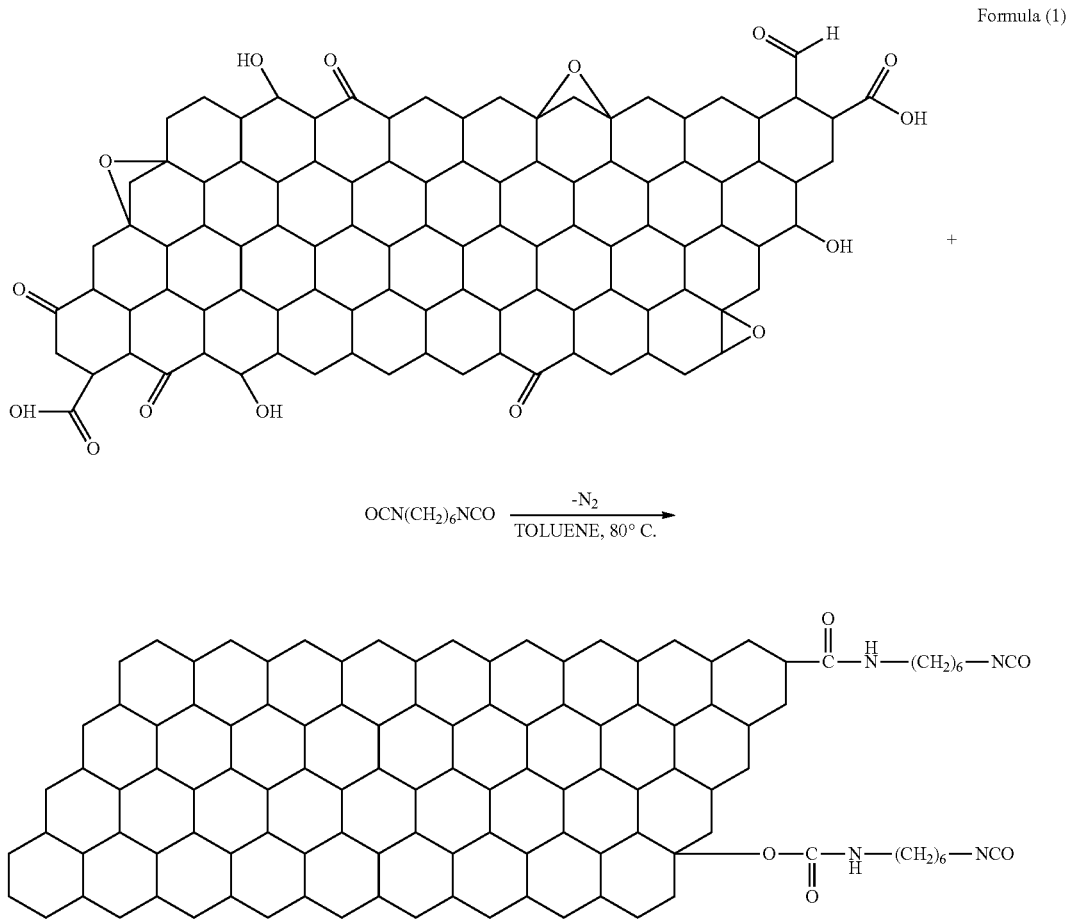

Formula (1)

As shown in the formula (1), a graphene-like carbon material, such as exfoliated graphite, has on a surface thereof a hydroxyl group and a carboxyl group. The hydroxyl group and carboxyl group each react with an isocyanate group of a diisocyanate compound so that the compound is bonded to the graphene-like carbon material. This can give an isocyanate-group-containing graphene-like carbon material, that is, an isocyanate-group-modified graphene-like carbon material of the present invention.

About the ratio between the graphene-like carbon material and the diisocyanate compound to be allowed to react with each other, the amount of the diisocyanate compound may be preferably set into the range of 100 to 1000 parts by weight relative to 100 parts by weight of the graphene-like carbon material. This range makes it possible to allow the graphene-like carbon material to react certainly with the diisocyanate compound.

The above-mentioned solvent that can be used includes various solvents such as toluene, xylene, cyclohexanone and methyl ethyl ketone. The heating temperature may be any temperature at which the diisocyanate compound reacts with a hydroxyl and/or carboxyl group. The temperature may be appropriately selected in accordance with the type of the diisocyanate compound. This heating temperature usually ranges from about 50 to 90° C.

The isocyanate-group-modified carbon material obtained according to the present invention is obtained by heating and stirring a graphene-like carbon material and a diisocyanate compound in a solvent as described above to allow them to react with each other. The thus obtained isocyanate-group-modified carbon material has, on the surface thereof, an isocyanate group. Accordingly, by using the reactivity of the isocyanate group, various modified carbon materials or composite materials can be obtained.

Examples of the composite materials include composite materials containing the above-mentioned isocyanate-group-modified carbon material and a resin.

Preferred examples of the application of the isocyanate-group-modified carbon material are described.

The isocyanate-group-modified carbon material is hydrolyzed, thereby making it possible to obtain an amino-group-modified carbon material. In an example thereof, the isocyanate-group-modified carbon material obtained at the right side of the formula (1) is hydrolyzed, thereby making it possible to obtain an amino-group-modified graphene-like carbon material as shown in the following formula (2):

[Chemical formula 2]

Formula (2)

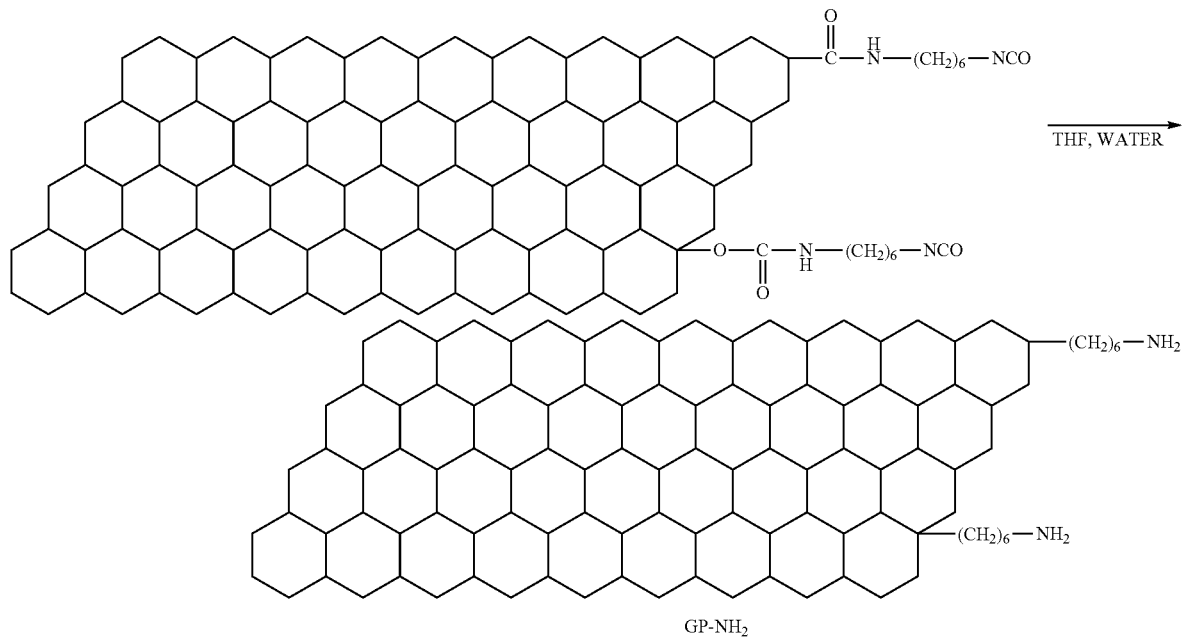

GP-NH₂

Moreover, the above-mentioned isocyanate-group-modified carbon material is allowed to react with a hydroxyl-group-containing compound such as a diol, thereby making it possible to form a urethane bond. It is therefore possible to not only produce a reinforcing effect based on the graphene-like carbon material, but also provide a composite material in which the graphene-like carbon material and a urethane resin matrix are excellent in adhesiveness onto each other.

(Amino-Group-Modified Graphene-Like Carbon Material)

The above-mentioned amino-group-containing azo-type radical initiator that can be used is an appropriate azo-type radical initiator which generates, when subjected to a treatment such as a heating or UV-radiating treatment, an amino-group-containing fragment that can be radical-decomposed. Examples of such an azo-type radical initiator include water-soluble radical initiators such as 2,2'-azobis[2-(2-imidazoline-2-yl)propane], and dihydrochloride of 2,2'-azobis(2-methylpropionamidine); and oil-soluble radical initiators such as 2,2'-azobis(2,4-dimethylvaleronitrile), and 2,2'-azobis[N-(2-propenyl)-2-methylpropionamide].

The amino-group-containing azo-type radical initiator that can be used is preferably, for example, 2,2'-azobis[2-(2-imidazoline-2-yl)propane], which has a structure represented by the following formula (3), or dihydrochloride of 2,2'-azobis(2-methylpropionamidine).

[Chemical formula 3]

Formula (3)

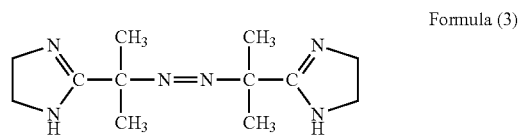

2,2'-Azobis[2-(2-imidazoline-2-yl)propane] represented by the formula (3) is dispersed in a solvent such as toluene and heated to a temperature of about 80° C., and thus is radical-decomposed as shown in a formula (4) shown below. The Radical-containing fragments as shown at the right side of the formula (5) are added to graphene by radical trapping, as shown at the right side of a formula (5).

It is therefore possible to add the amino-group-containing functional groups to graphene and provide a positively charged amino-group-modified carbon material.

[Chemical formula 4]

Formula (4)

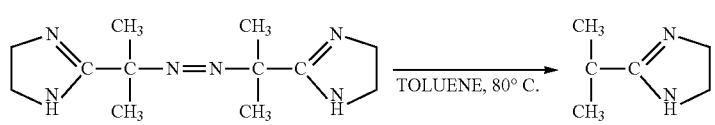

[Chemical formula 5]

Formula (5)

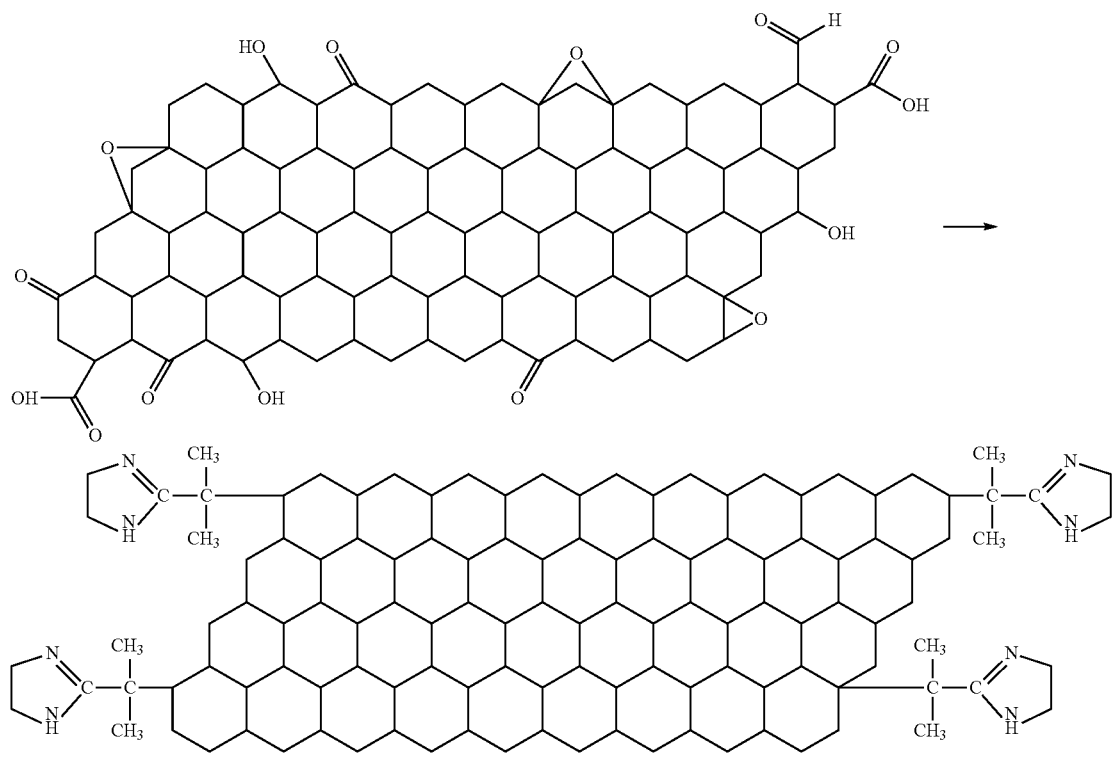

The above-mentioned amino-group-containing azo-type radical initiator may be an initiator having any of a primary amino group, a secondary amino group and a tertiary amino group. Preferably, the azo-type radical initiator to be used is an azo-type radical initiator having a secondary amino group, such as the compound represented by the formula (3); or an azo-type radical initiator having a tertiary amino group. In this case, merely by heating the initiator in a solvent, an amino-group-containing fragment can easily be generated which can be added to a graphene-like carbon material by radical trapping. Additionally, a larger number of amino groups can be introduced into the graphene-like carbon material.

About the ratio between the graphene-like carbon material and the amino-group-containing azo-type radical initiator to be allowed to react with each other, the amount of the amino-group-containing azo-type radical initiator may be preferably set into the range from 100 to 500 parts by weight relative to 100 parts by weight of the graphene-like carbon material. This range makes it possible to allow the graphene-like carbon material to react effectively and certainly with the amino-group-containing fragment.

The above-mentioned solvent that can be used includes various solvents such as toluene, xylene, dioxane, cyclohexanone and methyl ethyl ketone. The heating temperature may be any temperature at which the azo-type radical initiator is radical-decomposed. The temperature may be appropriately selected in accordance with the type of the azo-type radical initiator. When the azo-type radical initiator is an ordinary amino-group-containing azo-type radical initiator, this heating temperature ranges from about 70 to 90° C.

The amino-group-modified carbon material obtained according to the present invention is obtained by heating and stirring a graphene-like carbon material and an amino-group-containing azo-type radical initiator in a solvent as described above to allow them to react with each other. The thus obtained amino-group-modified carbon material has a positive charge originating from the amino group. Accordingly, when this amino-group-modified carbon material and, for example, a functional-group-containing polymer having on the surface thereof a negative charge are made into a composite material by, for example, the mixing of them, the amino-group-modified carbon material can be heightened in dispersibility in the polymer. In the case of mixing, in particular, fine particles made of a functional-group-containing resin having on the surface thereof a negative charge with the amino-group-modified carbon material in a solvent or dispersing medium to be made into a composite material, the amino-group-modified carbon material can be heightened in dispersibility. Accordingly, the fine particles made of the composite material of the fine resin particles and the amino-group-modified carbon material can be made high in physical property evenness.

The method for producing such fine particles made of a composite material of fine resin particles and the amino-group-modified carbon material is not particularly limited. In an example thereof, to water are added the amino-group-modified carbon material and an emulsion of a resin which contains a positively charged functional group such as a sulfonate group. The resultant is stirred to obtain a dispersion liquid. The thus obtained dispersion liquid is heated while stirred. By the heating, the water is removed to make it possible to obtain, for example, a composite material of the amino-group-modified carbon material and the functional-group-containing resin. Since the thus obtained composite material contains the amino-group-modified carbon material, the composite material can be made by far higher in thermal decomposition temperature than the original resin, which does not contain the amino-group-modified carbon material. In other words, the amino-group-modified carbon material is evenly dispersed in the positively charged resin, so that the composite material can be greatly heightened in heat resistance.

In the composite material of the amino-group-modified carbon material and the resin, it is preferred to use, as the resin, fine particles of the resin, as described above. In the above-mentioned composite material containing the isocyanate-group-modified carbon material and a resin, in the same manner, fine resin particles may be used as the resin.

The following will make the present invention clear with reference to specific Examples and Comparative Examples. The present invention is not limited to the following Examples.

EXAMPLE 1

A graphite sheet prepared as a raw material was a sheet (item number: PF100-UHP) manufactured by Toyo Carbon Co., Ltd. By the same method as used to produce this graphite sheet except that the rolling ratio in the rolling treatment therefor was lowered, prepared was a low-density graphite sheet having a density of 0.7 and a thickness of 1 mm.

The thus obtained graphite sheet, the density of which was 0.7, was cut into a size of 5 cm×5 cm to obtain a graphite sheet as an electrode material. A cutter knife was used to make two slits in this graphite sheet so as to give a slit length of 1 cm. An electrode made of Pt was inserted into this graphite sheet in which the two slits were made. The thus prepared graphite sheet was used as a working electrode (positive electrode). Together with a counter electrode (negative electrode) made of Pt and a reference electrode made of Ag/AgCl, the working electrode was immersed in an aqueous nitric acid solution, the concentration of which was 60% by weight. In the immersion of the graphite sheet of 5 cm×5 cm size, its region extending from the lower end of the sheet to a position thereof 4 cm in height was immersed in the aqueous nitric acid solution while the upper region of the graphite sheet was not immersed in the aqueous nitric acid solution. A direct current voltage was applied to perform electrochemical treatment. In this way, the region immersed in the aqueous nitric acid solution, in the original graphite sheet used as the working electrode, was changed to swelled graphite.

Next, the resultant swelled graphite was dried at a low temperature and then cut into pieces 1 cm square. One of the pieces was put into a carbon crucible to be subjected to electromagnetic induction heating treatment. Using an induction heating device, MU1700D, manufactured by SK Medical Electronics Co., Ltd., the treatment was conducted at a current of 14 A in an argon gas atmosphere to adjust the highest arrival temperature to 550° C. By the electromagnetic induction heating, the swelled graphite was made into the form of flakes. About the resultant exfoliated graphite powder, the specific surface area thereof was measured with a specific surface area measuring instrument, ASAP-2000, manufactured by Shimadzu Corp., using nitrogen gas. As a result, the powder exhibited a specific surface area of 1296 $m^2/g$ by one operation of the measurement.

To 1 g of the thus obtained exfoliated graphite (specific surface area: 1296 $m^2/g$) was added 5 mL of hexamethylene-1,6-diisocyanate. Together with 200 mL of toluene, the resultant was heated and stirred at 80° C. under a nitrogen atmosphere for 8 hours to introduce isocyanate groups into the exfoliated graphite.

FIG. 1 shows respective infrared spectra (thermal decomposition GC-MS) of the above-mentioned hexamethylene-1,6-diisocyanate, and an isocyanate-group-introduced exfoliated graphite obtained as described above.

Figure 2:
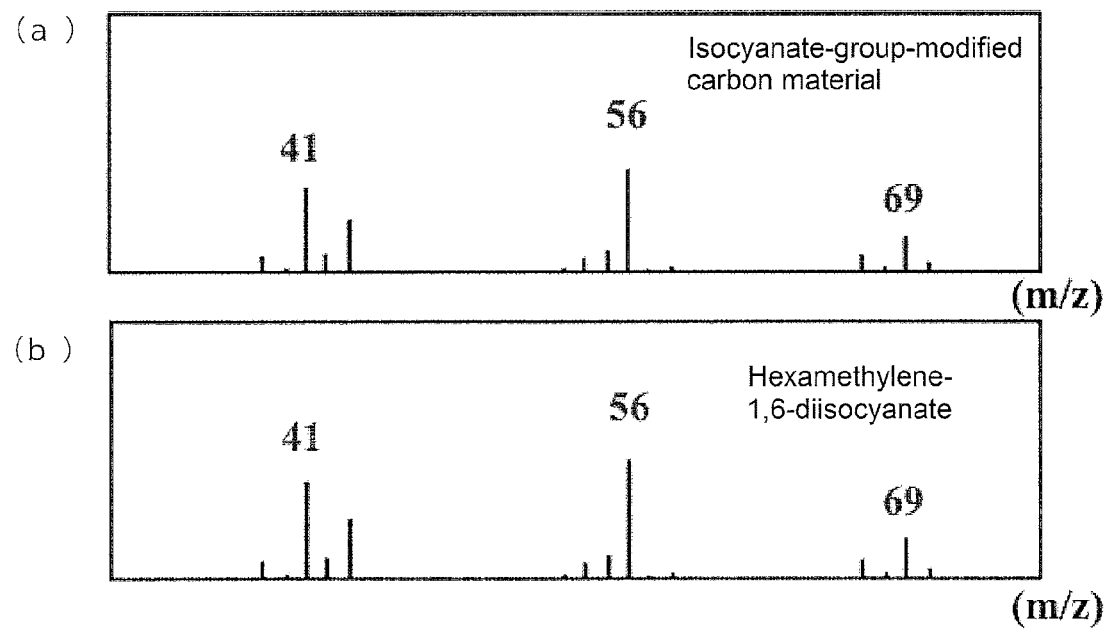
FIGS. 2(a) and 2(b) are charts showing mass spectra at the retention time of 4.52 minutes of respective thermal decomposition gases from the isocyanate-group-modified carbon material obtained in Example 1 and hexamethylene-1,6-diisocyanate.

FIG. 1 is a chart showing chromatograms of respective thermal decomposition gases from the isocyanate-group-modified carbon material obtained in Example 1, and hexamethylene-1,6-diisocyanate. According to FIG. 1, about the respective thermal decomposition gases from hexamethylene-1,6-diisocyanate and the isocyanate-group-modified carbon material, the production of common thermal decomposition gas was recognized at a retention time of 4.52 minutes. FIGS. 2(a) and 2(b) are charts showing mass spectra at the retention time of 4.52 minutes of respective thermal decomposition gases from the isocyanate-group-modified carbon material obtained in Example 1, and hexamethylene-1,6-diisocyanate. It is understood from FIG. 2 that the mass spectra at the retention time of 4.52 minutes of the respective thermal decomposition gases from hexamethylene-1,6-diisocyanate and the isocyanate-group-modified carbon material were completely consistent with each other and thus a fragment having an isocyanate group was added to the exfoliated graphite.

By a quantitative determination method of isocyanate groups prescribed in JIS K8006, a measurement was made about the quantity of isocyanate groups in the isocyanate-group-modified exfoliated graphite obtained as described above. The result thereof demonstrated that the isocyanate groups were bonded to the exfoliated graphite in an equivalent of 0.10 per gram of the exfoliated graphite.

EXAMPLE 2

In the same way as in Example 1 except that the exfoliated graphite as the carbon material was changed to oxidized graphite, an isocyanate-group-modified exfoliated graphite was obtained.

In the isocyanate-group-modified exfoliated graphite obtained as described above, the proportion of its isocyanate groups was analyzed in the same way as in Example 1. As a result, the proportion of the isocyanate groups was an equivalent of 0.01 per gram of the exfoliated graphite.

COMPARATIVE EXAMPLE 1

Into a 2-L polymerization vessel were charged 1100 mL of water and 180 mL of a styrene monomer. While nitrogen gas was introduced thereinto, the reaction system was stirred at a stirring speed of 180 rpm with a stirring blade to prepare an emulsion. Separately, prepared was a dispersing agent solution in which a p-styrenesulfonic acid monomer as a dispersing agent was diluted with water to give a concentration of 2% by weight. Prepared was also a polymerization initiator solution in which potassium peroxodisulfate as a polymerization initiator was diluted with water to give a concentration of 3% by weight.

The temperature of the emulsion was raised to 70° C. in the state that the introduction of nitrogen gas was kept. Thereafter, 20 mL of the polymerization initiator solution was added thereto, and subsequently 50 mL of the dispersing agent solution was added thereto. While the polymerization temperature was kept in the range of 70±2° C., the polymerization treatment was continued over 8 hours. In this way, an emulsion was obtained.

The emulsion was observed by TEM. As a result, it was confirmed that fine particles having a diameter of about 120 nm were dispersed.

Figure 5:
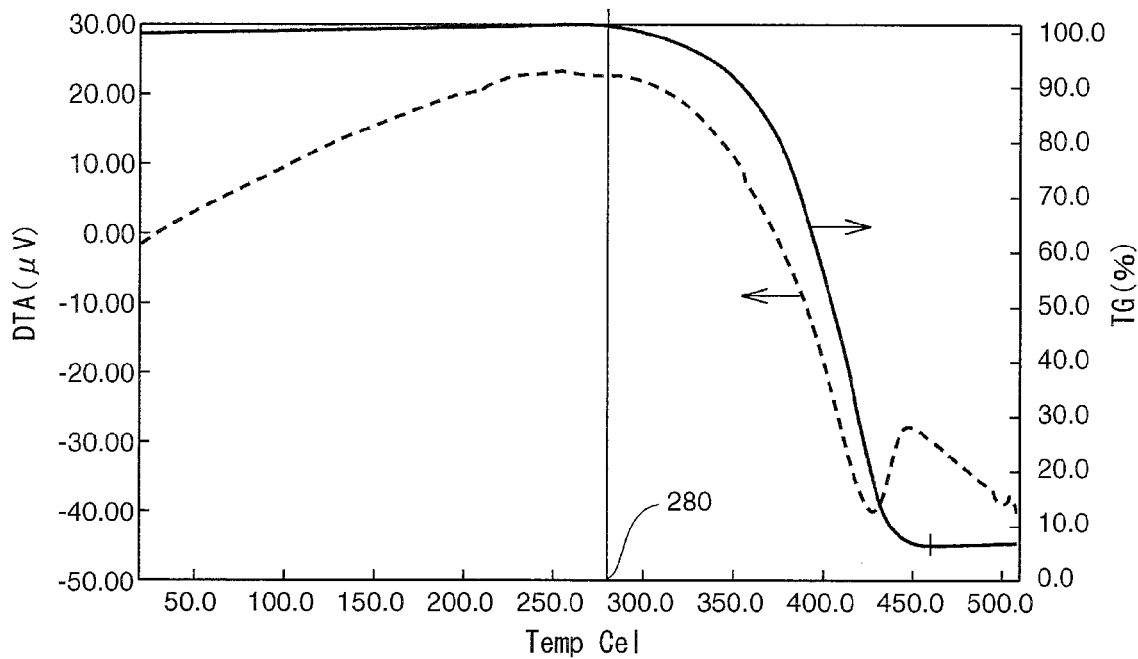
FIG. 5 is a chart showing a thermal analysis result of a composite material determined by TG-DTA, this material being obtained in Comparative Example 1 and made of an amino-group-modified carbon material and a resin.

Next, the resultant emulsion was vacuum-dried to remove water. In this way, a styrene-styrenesulfonic acid copolymer was obtained. The thermal decomposition temperature of the obtained copolymer was measured by TG-DTA. The result is shown in FIG. 5. As is evident from FIG. 5, the thermal decomposition starting temperature of the styrene-styrenesulfonic acid copolymer obtained in Comparative Example 1 was about 280° C.

EXAMPLE 3

Swelled graphite was supplied into between a pair of rolls, and then sheet-molded to prepare a graphite sheet having a density of 0.7 and a thickness of 1 mm.

The thus obtained graphite sheet, the density of which was 0.7, was cut into a size of 5 cm×5 cm to obtain a graphite sheet as an electrode material. A cutter knife was used to make two slits in this graphite sheet to give a slit length of 1 cm. An electrode made of Pt was inserted into this graphite sheet in which the two slits were made. The thus prepared graphite sheet was used as a working electrode (positive electrode). Together with a counter electrode (negative electrode) made of Pt and a reference electrode made of Ag/AgCl, the working electrode was immersed in an aqueous nitric acid solution, the concentration of which was 60% by weight. In the immersion of the graphite sheet of 5 cm×5 cm size, its region extending from the lower end of the sheet to a position thereof 4 cm in height was immersed in the aqueous nitric acid solution while the upper region of the graphite sheet was not immersed in the aqueous nitric acid solution. A direct current voltage was applied to perform electrochemical treatment. In this way, the region immersed in the aqueous nitric acid solution, in the graphite sheet used as the working electrode, was changed to swelled graphite.

Next, the resultant swelled graphite was dried at a low temperature and then cut into pieces 1 cm square. One of the pieces was put into a carbon crucible to be subjected to electromagnetic induction heating treatment. Using an induction heating device, MU1700D, manufactured by SK Medical Electronics Co., Ltd., the treatment was conducted at a current of 14 A in an argon gas atmosphere to adjust the highest arrival temperature to 550° C. By the electromagnetic induction heating, the swelled graphite was made into the form of flakes. About the resultant exfoliated graphite powder, the specific surface area thereof was measured with a specific surface area measuring instrument, ASAP-2000, manufactured by Shimadzu Corp., using nitrogen gas. As a result, the powder exhibited a specific surface area of 1296 $m^2/g$ by one operation of the measurement.

In 200 mL of toluene, 1.0 g of the thus obtained exfoliated graphite and 4.0 g of 2,2'-azobis[2-(2-imidazoline-2-yl)propane] represented by the formula (1) as an azo-type radical initiator were heated and stirred under a nitrogen atmosphere at a temperature of 80° C. In this way, an amino-group-modified carbon material was obtained.

Figure 3:
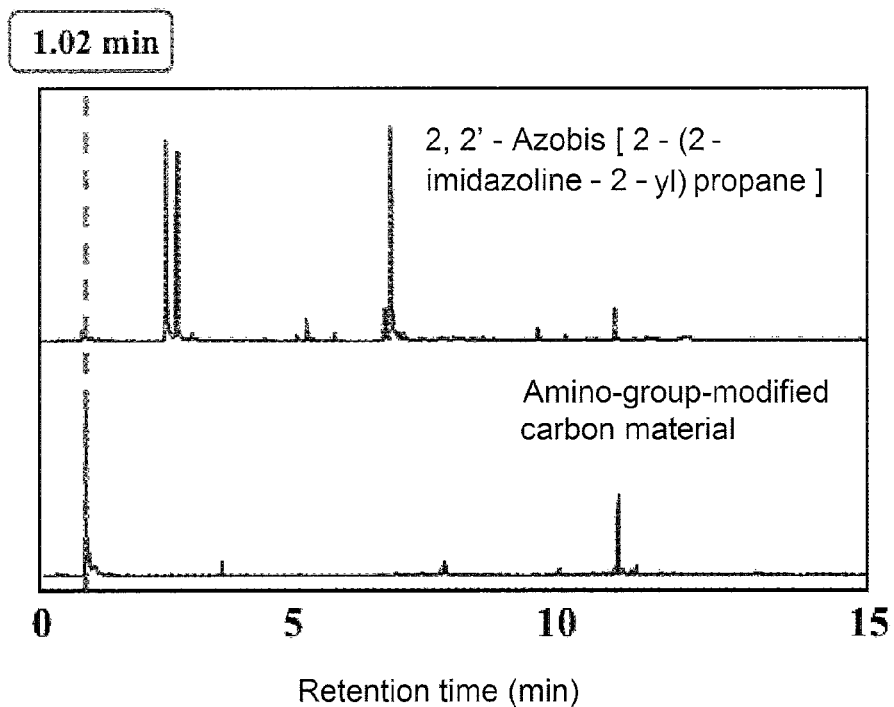
FIG. 3 is a chart showing chromatograms of respective thermal decomposition gases from 2,2'-azobis[2-(2-imidazoline-2-yl)propane] and an amino-group-modified carbon material obtained in Example 3.
Figure 4:
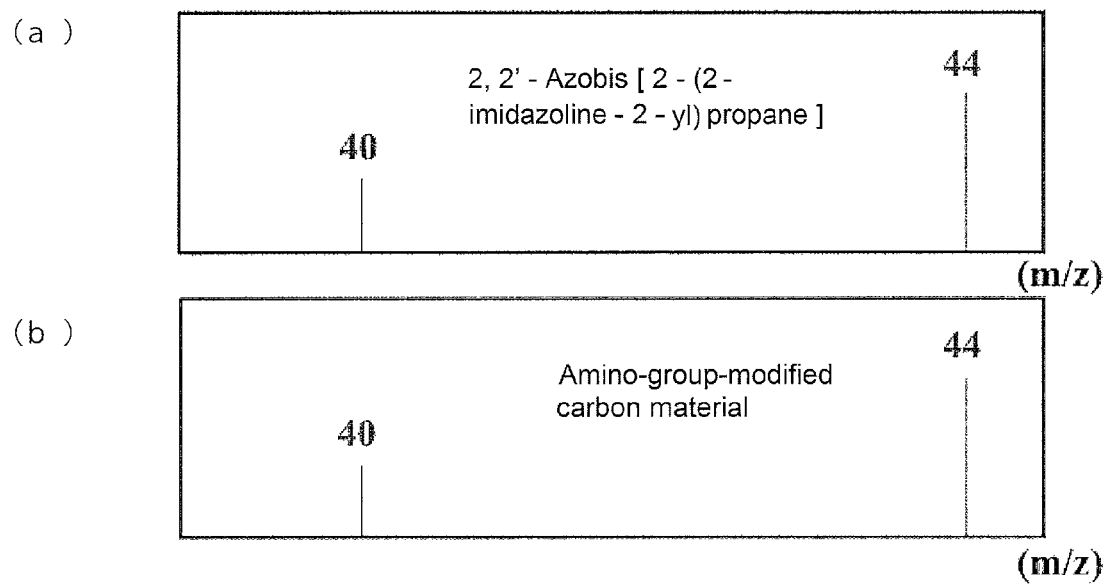
FIGS. 4(a) and 4(b) are charts showing mass spectra of at the retention time of 1.02 minutes of respective thermal decomposition gases from 2,2'-azobis[2-(2-imidazoline-2-yl)propane] and the amino-group-modified carbon material obtained in Example 3.

FIG. 3 is a chart showing chromatograms of respective thermal decomposition gases from 2,2'-azobis[2-(2-imidazoline-2-yl)propane] and the amino-group-modified carbon material obtained in Example 3. According to FIG. 3, about the respective thermal decomposition gases from 2,2'-azobis [2-(2-imidazoline-2-yl) propane] and the amino-group-modified carbon material, the production of common thermal decomposition gas was recognized at a retention time of 1.02 minutes. FIGS. 4(a) and 4(b) are charts showing mass spectra at the retention time of 1.02 minutes of the respective thermal decomposition gases from 2,2'-azobis[2-(2-imidazoline-2-yl)propane] and the amino-group-modified carbon material obtained in Example 3. It is understood from FIGS. 4(a) and 4(b) that the mass spectra at the retention time of 1.02 minutes of the respective thermal decomposition gases from 2,2'-azobis[2-(2-imidazoline-2-yl)propane] and the amino-group-modified carbon material were completely consistent with each other and thus a fragment having an amino group was added to the exfoliated graphite.

Into 10 g of water was dispersed 15 g of the thus obtained amino-group-modified carbon material to succeed in obtaining a dispersion liquid of exfoliated graphite in water which was excellent in dispersibility. Separately, an emulsion as produced in Comparative Example 1 was prepared to give a solid concentration of 10% by weight. The emulsion was added to the dispersion liquid of exfoliated graphite in water to adjust the amount of solid in the prepared emulsion to 0.57 g, and the resultant was stirred. The dispersion state of the emulsion and the exfoliated graphite was good. The thus obtained dispersion liquid was vacuum-dried and heated at 100° C. to remove water. As a result, a homogeneous, black and transparent resin composite material was obtained. In light of the charged components, this composite material was a composite material of a styrene-sodium styrene sulfonate copolymer and amino-group-modified exfoliated graphite.

Figure 6:
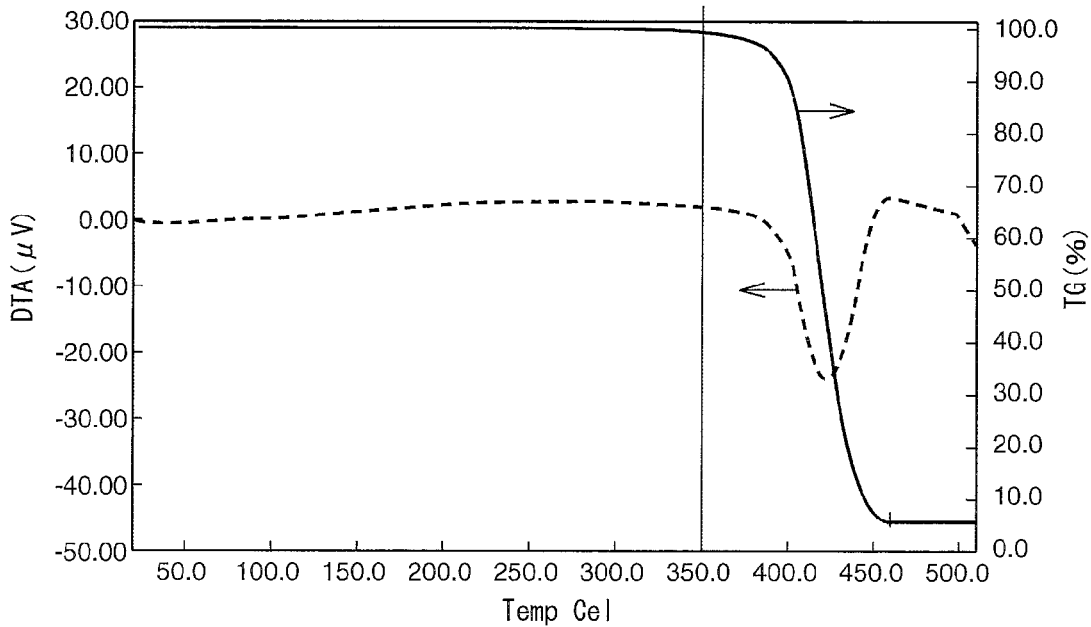
FIG. 6 is a chart showing a thermal analysis result of a composite material determined by TG-DTA, this material being obtained in Example 3 and made of a carbon material and a resin.

The thermal decomposition temperature of the composite material obtained in the above-mentioned way was measured by TG-DTA in the same manner as in Comparative Example 1. The result is shown in FIG. 6. As is evident from FIG. 6, the thermal decomposition starting temperature was about 350° C. By a comparison between this temperature and about 280° C., which was that in Comparative Example 1, it is understood that this example was made higher in heat resistance than Comparative Example 1 by about 70° C. or more.

The invention claimed is:

1. A functional-group-modified carbon material, a fragment obtained by radical-decomposing an amino group-containing azo-type radical initiator being added to exfoliated graphite by radical-trapping,
   wherein the exfoliated graphite is a laminate of plural graphene layers that is obtained by peeling off flakes from non-oxidized ordinary graphite and is a material in which the number of graphene layers laminated is from several to about 200 and the specific surface area is from about 600 to 2500 $m^2/g$.

2. A method for producing a functional-group-modified carbon material, comprising: heating and stirring, in a solvent, exfoliated graphite, and an amino-group-containing azo-type radical initiator,
   wherein the exfoliated graphite is a laminate of plural graphene layers that is obtained by peeling off flakes from non-oxidized ordinary graphite and is a material in which the number of graphene layers laminated is from several to about 200 and the specific surface area is from about 600 to 2500 $m^2/g$.

3. The method for producing a functional-group-modified carbon material according to claim 2, wherein the azo-type radical initiator is an azo-type radical initiator having a secondary or tertiary amino group.

4. A composite material comprising the functional-group-modified carbon material according to claim 1, and a resin.

5. The composite material according to claim 4, wherein the resin is in the form of resin fine particles.

* * * * *